United States Patent [19]

Baker et al.

[11] Patent Number: 4,985,462
[45] Date of Patent: Jan. 15, 1991

[54] ALICYCLIC COMPOUNDS AND THEIR CONTRACEPTIVE USE

[75] Inventors: James A. Baker, Brighton; Stuart L. James, Seaford; Tuncel Ibrahim, Abingdon; Christopher Marriott, Lewes, all of England

[73] Assignee: National Research Development Corporation, London, England

[21] Appl. No.: 435,479

[22] PCT Filed: May 24, 1988

[86] PCT No.: PCT/GB88/00408

§ 371 Date: Dec. 4, 1989

§ 102(e) Date: Dec. 4, 1989

[87] PCT Pub. No.: WO88/09786

PCT Pub. Date: Dec. 15, 1988

[30] Foreign Application Priority Data

Jun. 2, 1987 [GB] United Kingdom ................. 8712948

[51] Int. Cl.$^5$ ..................... A61K 31/16; C07C 235/32
[52] U.S. Cl. ...................................... 514/623; 564/188
[58] Field of Search .......................... 564/188; 514/623

[56] References Cited

U.S. PATENT DOCUMENTS 2,862,953 12/1958 Abe et al. .............................. 564/188
3,941,836 3/1976 Coleman ............................... 564/188

FOREIGN PATENT DOCUMENTS 1357628 3/1964 France ................................. 564/188

OTHER PUBLICATIONS

V. B. Piskov, Tr. Gos. Nauch.—Kontrol'n. In-Ta Vet. Preparatov. 20, 288–293 (1974) (translation enclosed).
C. Marriott and I. W. Kellaway, Biorheology 12, 391–395 (1975).
S. S. Davies and L. C. Deverell, Mod. Prob. Pediat. 19, 207–217 (1977).
V. P. Kamboj et al., Indian J. Exp. Biol 17, 1379–1380 (1977).
M. Saga et al., St. Marianna Med. J. 7, 146–150 (1979).

Primary Examiner—Glennon H. Hollrah
Assistant Examiner—S. Treanor
Attorney, Agent, or Firm—Nixon & Vanderhye

[57] ABSTRACT

Compounds of the general formula

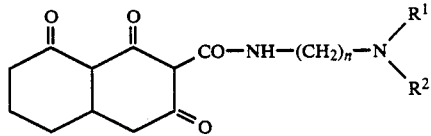

wherein n is from 1 to 6 and each of $R^1$ and $R^2$ represents an alkyl group of 1 to 4 carbon atoms and their acid addition salts are useful for thickening mucus, especially gastro-intestinal mucus as an anti-ulceration treatment or cervical mucus in contraception.

11 Claims, No Drawings

ALICYCLIC COMPOUNDS AND THEIR CONTRACEPTIVE USE

BACKGROUND OF THE INVENTION

1. Field of the invention

This invention relates to alicyclic compounds useful in topical contraception. They appear to have a predominantly spermicidal action, but to some extent also have a mucospissic (mucus-thickening) effect which inhibits the movement of sperm in the cervical canal. The mucus-thickening effect enables the compounds to be used for various therapeutic purposes.

2. Description of prior art

Mucus is secreted in many different parts of the human body. For example, the stomach has a thick lining of mucus which protects the epithelial cells from attack. Damage to the mucus lining is believed to play a part in gastric ulceration. It is also secreted in the cervix where it has an important role in conception. In the middle of the menstrual cycle the mucus has low visco-elasticity, favouring penetration of sperm at a time which is essential for conception, but at other times in the cycle it thickens and thereby acts to some extent as a natural contraceptive by impeding the passage of sperm to the womb. It would be desirable to thicken gastric mucus to counteract ulcers and also cervical mucus for the purposes of contraception. The latter objective has taken on greater importance in view of the increasing use of the protective sheaths brought about by the fear of acquired immune deficiency syndrome (AIDS). The use of an agent for thickening cervical mucus would provide an additional barrier to sperm, either instead of or in addition to a spermicidal agent.

Relatively little research has been devoted to additives for thickening mucus. C. Marriott and I.W. Kellaway. Biorheology 12, 391–395 (1975) reported that tetracycline and three derivatives thereof increased the thickness of bronchial mucus. S.S. Davis and L.C. Deverell, Mod. Probl. Pediat. 19, 207–217 (1977), showed that sodium tetraborate. Congo red and tetracycline are mucospissic agents. V.P. Kamboj et al., Indian J. Exp. Biol. 17, 1379–1380 (1977) showed that various plant extracts reduced the migration of sperm through cervical mucus. M. Saga et al., St. Marianna Med. J. 7, 146–150 (1979) have showed that calcium ions, spermine, polylysine and lysozyme all thicken human cervical mucus. These authors claim that these highly basic, cationic additives interact with acidic, negatively charged mucin molecules. According to L. Batallan et al.. Contraception-fertilité-sexualité 8, 735–739 (1980), the modern era of vaginal chemical contraception began with surfactants, with the introduction of a spermicide containing dimethyl alkyl benzyl ammonium chloride. Experiments by Batallon et al. on this spermicide indicated that this compound might act to modify the structure of the cervical mucus. U.S. Pat. No. 4,590.070 (Chantler et al. assigned to ICI) claims a contraceptive method depending on the application to the vagina of a linear polymer of formula —X.NH.C(=NH) NH.C(=NH). NH.Y. NH.C(=NH). NH.C(=NH)NH— wherein X and Y are bridging groups in which together the total number of carbon atoms directly interposed between adjacent nitrogen atoms is greater than 9 and less than 17, or an acid addition salt thereof.

It has been a problem to provide an alternative contraceptive agent.

Further prior art is discussed after the "Summary of the invention", without which its context would not be clear.

SUMMARY OF THE INVENTION

It has now been found that compounds of the general formula (1):

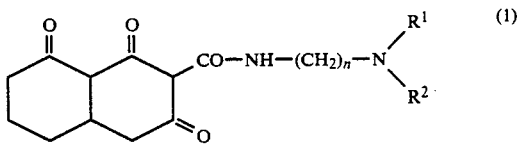

wherein n is from 1 to 6 and each of $R^1$ and $R^2$ represents an alkyl group of 1 to 4 carbon atoms, and their acid addition salts are useful in topical contraception whereby sperm are killed or immobilised or their movement through the cervical canal is inhibited. In the above formula n is preferably 1 to 3, most preferably 2 and $R^1$ and $R^2$ are preferably the same and are preferably methyl or ethyl.

FURTHER DESCRIPTION OF PRIOR ART

This invention has been searched by the European Patent Office during the priority year. The Search Report, ref. RS 78871 GB, cited only one document, viz. French Patent Specification 1,357,628 (Pfizer). This reference refers to a vast class of polycyclic compounds as useful as chelates, sequestrants and complexing agents. Included within this vast class are compounds of formula (2):

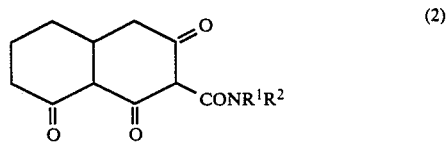

where $R^1$ is lower alkyl substituted by di(lower alkyl) amino and $R^2$ is hydrogen. However, the reference does not mention any $R^1$ groups which are straight chain alkyl and indeed says at page 2, right-hand column, middle that in a preferred class of compounds $R^1$ is a secondary or tertiary alkyl group. This preference is confirmed by the Examples, in which $R^1$ is t-butyl (unsubstituted).

The compound of formula (2) in which $R^1$ is t-butyl and $R^2$ is hydrogen, disclosed in Example 3 of the French Patent Specification, is also disclosed in a Russian language paper V.B. Piskov. Tr. Gos. Nauch.—Kontrol'n. In-Ta Vet. Preparatov 20 288–293 (1974). The paper is wholly concerned with synthesis of tetracyclines and suggests no uses for the compound.

DESCRIPTION OF THE PREFERRED EMBODIMENTS

The compounds of the invention include free amine bases and their acid addition salts. Either the base or a salt can be used depending on the required pH and convenience of handling. Salts include those formed with organic acids such as citrates and acetates and with inorganic acids such as hydrochlorides, sulphates and phosphates.

The compounds of the invention can be prepared from the known compound 3-oxocyclohexylacetic acid by a process which comprises the following steps:

(1) preparing an acid halide or mixed anhydride of 3-oxocyclohexylacetic acid by reacting it with a halogenating agent or an ester of chloroformic acid thereby forming a compound of general formula (3):

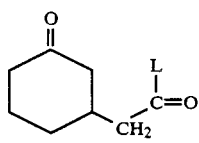
(3)

wherein L represents chlorine, bromine, or an anhydride residue of formula —O—CO—O—$R^3$, $R^3$ being a hydrocarbyl group, preferably alkyl of 1 to 4 carbon atoms, (2) reacting the compound of formula (3) with a malonate derivative providing a nucleophilic reagent of formula $R^4OOC$—$\overline{CH}$—$COR^5$ wherein $R^4$ represents an alkyl group having 1 to 3 carbon atoms, preferably ethyl, or an aralkyl group, preferably benzyl or 2-phenylethyl, and $R^5$ represents —$OR^4$ or the residue of an amide group, said malonate derivative preferably being ethoxymagnesium dialkyl malonate, thereby forming a compound of formula (4):

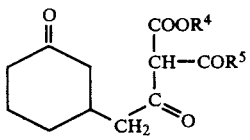
(4)

wherein $R^4$ is as defined above, (3) cyclising the compound of formula (4) under strongly basic, but non-deacylating, conditions, preferably with sodium hydride to give a 1,3,8-trioxodecahydronaphthalene-2-carboxylic ester or carboxamide of formula (5):

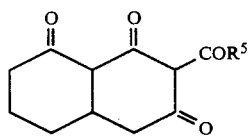
(5)

wherein $R^5$ is as defined above, (4) reacting the ester or the amide (unless, of course, $R^5$=NH—$(CH_2)_n NR^1R^2$, in which case step (4) is omitted) with an amine of general formula (6):

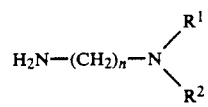
(6)

wherein n, $R^1$ and $R^2$ are as defined in formula (1), to yield a compound of formula (1), and (5) when an acid addition salt is required, reacting the free base of formula (1) with an acid.

In the above-described process of preparation, step (1) involves derivatising the starting acid to provide a reactive derivative in which the —OH of its carboxylic acid group is replaced by a good leaving group L. Any of the standard halogenating agents, for example oxalyl chloride or bromide, phosphorus pentachloride or thionyl chloride, can be used to provide an acid halide. Alternatively, a chloroformic acid ester, typically a $C_{1-4}$ alkyl, preferably isobutyl, chloroformate, is used to prepare a mixed anhydride. In step (2) a malonic acid diester or half-ester, half-amide is used, the malonic residue displacing the leaving group L. When a half-amide group is present it can be of virtually any kind e.g. NH-alkyl or N,N-dialkyl in which the alkyl group can be substituted or unsubstituted. In step (3) the objective is to carry out a quasi-Dieckmann condensation reaction with ring closure but while retaining the $COR^5$ group for the reaction in step (4). For that purpose the conventional use of sodium ethoxide in ethanol cannot be recommended because the malonate residue (7):

(7)

would be deacylated.

The compounds of the invention are primarily useful in a topical method of contraception, which comprises applying the compound in a sperm migration-inhibiting amount in any manner in which it will reach the cervix and thereby exert a contraceptive effect. An effective amount of compound is typically that which maintains a concentration in the range 0.5 to 20 millimolar, preferably 1 to 15 millimolar, in the mucus. An appropriate amount to apply to the cervix is from 0.3 to 6 mg./day. It can be administered directly to the upper region of the vagina or in any manner known for spermicidal preparations, for example in conjunction with a protective sheath or cervical cap ("Dutch cap"). For this purpose, it is conveniently formulated together with an appropriate non-toxic carrier, as a cream or ointment. Any of the usual emulsifying ingredients can be employed for formulating a cream or ointment. An alternative formulation is as in a pessary, whereby the compound of the invention is released in small amounts over an extended time. Preferably a sustained or controlled release device or formulation is used, for example a cervical ring pessary, or a polymer matrix in which the active ingredient is releasably suspended in or chemically bonded to, the polymer. Such pessaries can be formulated as controlled release compositions using as an excipient a polymeric carrier comprising residues which are cross-linked through urethane groups and which comprise polyethylene oxide, as described in UK Patent Specification 2047093A (National Research Development Corporation). Application can also be by way of an aerosol. An aerosol formulation comprises the compound of the invention, a carrier and a propellant under pressure.

The compounds of the invention can be formulated together with a reagent for adjusting the vaginal pH, as described in PCT Application WO 87/01585 (Affiliated Innovation Management Inc. of Tampa, FL USA). This patent application also describes vaginal tablets, capsules, pessaries and suppositories; they can also be used in the present invention with or without the pH-adjusting agent, as desired.

It will be appreciated that the compounds of the invention could be applied to the cervix by couples already incapable of conception (e.g. through vasectomy or hysterectomy) as a precaution against transmission of viral or bacterial agents through the cervix, in particular for inhibiting pelvic inflammatory disease. For the last-mentioned purpose the compounds of the invention are conveniently incorporated in the marker tail of an intra-uterine contraceptive device.

The mucus-thickening effect of the compounds of the invention suggests their use for other purposes than contraception. Obviously, acid addition salts of the invention must be pharmaceutically acceptable for the mode of administration intended and the compounds must be administered in a dose effective for the specified purpose. Thus, for use as an anti-ulcer agent, e.g. for the oesophagus, stomach or duodenum, either therapeutically or prophylactically as a cytoprotectant, the compounds of the invention can be formulated as a pill, tablet, lozenge, capsule or other orally administrable form, in any conventional manner. A suggested dose for these purposes is from 5 to 100 mg/day.

The compounds of the invention can also be administered rectally, e.g. by suppository or enema, to treat colitis or diverticulitis.

Another use of the compounds of the invention is for inclusion in eyedrops for treating the condition known as "dry eye".

The following Examples illustrate the invention. Temperatures are in degrees Celsius.

EXAMPLE 1

Synthesis of N-(2-dimethylaminoethyl)-1,3,8-trioxodecahydronaphthalene-2-carboxamide hydrochloride This synthesis was accomplished according to the following scheme:

Mixed anhydride (10) from 3-oxocyclohexylacetic acid (8) and isobutyl chloroformate (9)

A solution of 3-oxocyclohexylacetic acid (1.56 g., 10 mmole) in dichloromethane (20 ml) was treated with triethylamine (1.5 ml; 10.8 mmole) and the mixture cooled in ice. Isobutyl chloroformate (1.5 ml; 11.4 mmole) dissolved in dichloromethane (6 ml) was then added and the mixture left in ice, with an occasional swirl, for 80 min. After the addition of ice-cold water (10 ml) the organic layer was separated, rapidly washed with ice-cold water (2×15 ml) and dried (MgSO4) for 3 hr. Removal of the desiccant and solvent (rotary evaporator, 40°) gave the anhydride.

Ethyl 2-ethoxycarbonyl-3-oxo-4-{3-oxocyclohexyl)butanoate (11)

The foregoing anhydride was added to a solution of the ethoxymagnesium derivative of diethyl malonate (prepared from diethyl malonate (1.5 ml; 10 mmole) and magnesium (0.243 g; 10 mmole) in acetonitrile (20 ml) and the solution set aside for 18 hr or refluxed for 2 hr. The solvent was then removed (rotary evaporator; 55°). A solution of the resulting transparent flaky solid in dichloromethane (20 ml) was extracted with ice-cold dilute hydrochloric acid (3×20 ml) followed by water (3×20 ml). After drying (MgSO4) the organic layer for 3 hr, the desiccant and solvent were removed (rotary evaporator; 95°) to give 2.85 g (96%) of the ester as a very pale yellow oil with a fruity odour.

Ethyl 1,3,8-trioxodecahvdronaphthalene-2-carboxylate (12)

Sodium hydride in oil (60%, 24 g, 0.6 mole) was washed portionwise with petroleum spirit (60°-80°; dried over CaH2; 250 ml) in an atmosphere of nitrogen.

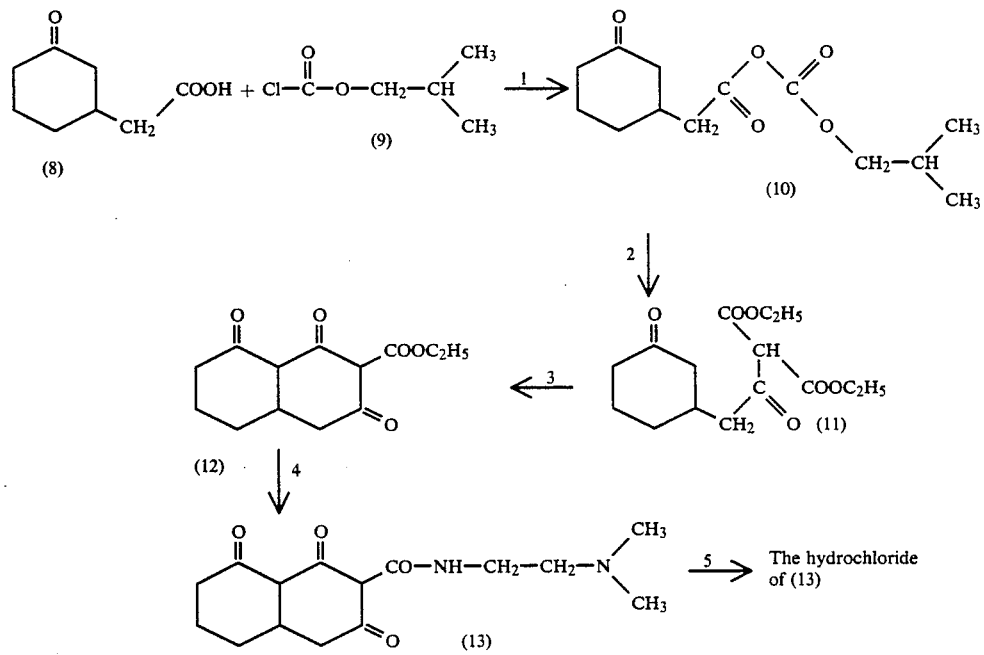

1. N(C2H5)3, CH2Cl2,
2. Ethoxymagnesium derivative of diethyl malonate, CH3CN,
3. NaH, toluene,
4. H2N—CH2—CH2—N(CH3)2, benzene,
5. HCl.

The sodium hydride was then covered with toluene (Na dried; 150 ml) and the mixture heated to vigorous reflux while being stirred mechanically. A solution of the diester (11) (30 mmoles) in toluene (Na dried, 60 ml), containing superdry ethanol (10 drops) was added during 6 min and reflux continued for a further 54 min. After cooling the mixture in ice, the excess sodium hydride was decomposed by the slow addition of glacial acetic acid (45 ml) followed by water (100 ml). The aqueous layer was removed, the toluene layer washed with water (50 ml) and the combined aqueous layers were extracted with toluene (25 ml). The combined toluene layers were then extracted with a freshly prepared solution of sodium bicarbonate (24 g) in water (360 ml). Extraction was repeated twice more with sodium bicarbonate (12 g) in water (180ml). Filtration, followed by acidification with concentrated hydrochloric acid, of the bicarbonate extracts yielded 2.01 g (26.6%) of crude (12). Crystallisation from hexane (charcoal) gave a cream product m.p. 90.5°–93.5°.

N-(2-dimethylaminoethyl)-1,3,8-trioxodecahydronaphthalene-2-carboxamide hydrochloride (13 hydrochloride)

N,N-Dimethylethylenediamine (1.5 ml; 13.7 mmole) was added to a solution of ester (12) (757 mg, 3 mmole) in benzene (10 ml) and the mixture set aside in the dark for 6 days. A gum deposited. The solvent was removed (rotary evaporator; 80°) and the residue dissolved in dilute hydrochloric acid (14 ml) plus water (40 ml). After treatment with acid-washed charcoal, the solution was evaporated to dryness. The residue, after crystallisation thrice from ethanol, yielded 440 mg (44%) of (13) hydrochloride, m.p. 220°–221° decomp.

EXAMPLE 2

Tests for mucospissic activity of N-(2-dimethylaminoethyl)-1,3,8-trioxodecahydronaphthalene-2-carboxamide (13)

The mucospissic activity of compound (13) was investigated using purified pig gastric mucus glycoprotein as a model gel. Gastric mucus is both biochemically and structurally similar to cervical mucus and is readily available in large quantities. The crude mucus is easy to purify and provides a glycoprotein gel of better defined composition than the native secretion.

Preparation and Purification of Mucus Samples

Mucus samples were collected by gently scraping the luminal surface of stomachs removed from freshly slaughtered pigs. The collected gel was pooled and solubilised in an equal volume of double strength phenylmethylsulphonylfluoride (PMSF) protease inhibiting solution. The solubilised gel material was centrifuged at high speed, the supernatant was filtered, and the filtrate applied to "Sepharose" CL-4B gel filtration columns at 4°. The eluate was monitored spectrophotometrically at 280 nm and the excluded fraction corresponding to the first major absorbance peak collected. The main non-glycoprotein contaminants such as non-covalently bound protein, lipids and sugars are mostly included on "Sepharose" CL-4B and eluted as a secondary peak which was discarded. Following exhaustive dialysis at 4° against 5 mM Tris HCl buffer at pH 7.2, the purified glycoprotein solution was concentrated to a gel by ultrafiltration and the dry weight determined. Sample aliquots were adjusted with an appropriate quantity of the buffer to yield gels of the same % w/w composition but including a desired test concentration of compound (13), added as the hydrochloride, or buffer alone in the control. The pH of each solution was checked before addition to the gel. Samples were prepared in duplicate and after gentle mixing, allowed to equilibrate overnight at 4° to ensure homogeneity.

The majority of rheological analysis was conducted using an oscillating sphere magnetic microrheometer. However, further verification of the mucospissic activity of compound (13) was obtained by creep compliance testing.

Rheological Determination of Mucus Viscoelasticity

Oscillating sphere magnetic microrheometer

An oscillating sphere magnetic microrheometer as described by S.L. James and C. Marriott. J. Phys. E. : Sci. Instrum. 15, 179–180 (1982), was used. Approximately 20 microliters of 8% w/w mucus gel were placed in a transparent well, and a 200 micrometre soft iron sphere completely immersed at the centre of the sample. The remainder of the well was filled with silicone oil to prevent desiccation of the gel during analysis. After a 20 minute equilibration period, the sample holder was positioned between the poles of two pairs of electro-magnets. A sinusoidally varying field gradient was produced across the sample, producing an oscillatory movement of the iron sphere within the gel. The image of the sphere was magnified by an optical microscope and projected so as to partially obscure a silicon solar photocell. A frequency response analyser compared the sinusoidal wave form being received by the photocell to that supplied to the electromagnets. This provided values for the phase lag and amplitude ratio (R) at discrete frequency intervals between 0.2 and 20 Hz. Mucus viscoelasticity was expressed in terms of the storage modulus (G') and the loss modulus (G") calculated at each frequency using the relationships:

$$G' = \left(\frac{F_o}{6\pi r \chi_o}\right)\cos\theta \text{ and } G'' = \left(\frac{F_o}{6\pi r \chi_o}\right)\sin\theta$$

where
$F_o$ = amplitude of the maximum magnetic force acting on the sphere
$r$ = sphere radius
$X_o$ = the maximum displacement of the sphere, where $X_o$ is a function of R.

The effect of compound (13) on the rheological properties of mucus was assessed at 1 mM, 4 mM and 8 mM concentrations on a number of different batches of gastric mucus at pH 7.2.

The storage modulus G', which is a measure of the elasticity of the sample and the loss modulus G", which is a measure of its viscosity both increase with increasing frequency of oscillation. The loss modulus reaches a plateau, which indicates that the gel structure is breaking down under the severe oscillation conditions at the 20 Hz frequency. The results, shown in Tables 1 and 2 below are for values of G' and G" in dynes cm.$^{-2}$, which are expressed as the means of at least 8 sample measurements, and for the frequency in Hertz.

TABLE 1

| | Samples | Frequency (Hz) Storage modulus (G') and loss modulus (G'') (dynes cm.$^{-2}$) | | | | | | | |
|---|---|---|---|---|---|---|---|---|---|
| | | 20 | 10 | 5 | 2.5 | 1.25 | 0.6 | 0.3 | 0.2 |
| G' | Control | 225 | 126 | 93 | 74 | 60 | 50 | 42 | 38 |
| | 1mM(13) | 303 | 179 | 133 | 106 | 88 | 71 | 60 | 55 |
| G'' | Control | 67 | 67 | 51 | 40 | 30 | 23 | 18 | 15 |
| | 1mM(13) | 100 | 98 | 72 | 54 | 43 | 32 | 25 | 21 |

TABLE 2

| | Samples | Frequency (Hz) Storage modulus (G') and loss modulus (G'') (dynes cm.$^{-2}$) | | | | | | | |
|---|---|---|---|---|---|---|---|---|---|
| | | 20 | 10 | 5 | 2.5 | 1.25 | 0.6 | 0.3 | 0.2 |
| G' | Control | 378 | 235 | 174 | 143 | 123 | 104 | 94 | 85 |
| | 4mM(13) | 602 | 368 | 271 | 218 | 184 | 159 | 142 | 132 |
| | 8mM(13) | 487 | 301 | 233 | 183 | 159 | 136 | 121 | 113 |
| G'' | Control | 89 | 94 | 80 | 60 | 46 | 35 | 28 | 25 |
| | 4mM(13) | 145 | 159 | 116 | 92 | 73 | 56 | 44 | 38 |
| | 8mM(13) | 117 | 128 | 103 | 74 | 56 | 45 | 37 | 31 |

From the above results it will be seen that the samples of mucus containing compound (13) were more viscous and more elastic than the control samples not containing compound (13), the difference becoming apparent with increasing frequency of oscillation. The differences between the two sets of data for the control sample are ascribed to batch to batch variation of composition or properties of the mucus sample.

Creep compliance rheometer

The mucospissic action of compound (13) was also investigated using a creep compliance rheometer as described by C. Marriott et al.. J. Phys. E. : Sci. Instrum. 6, 200–201 (1973). Test details and the results indicating the pronounced mucospissic activity of this compound, are given in the priority document, but omitted here in the interests of brevity.

EXAMPLE 3

Tests for sperm migration inhibitory activity of N-(2-dimethylaminoethyl)-1,3,8-trioxodecahydronapthalene2-carboxamide (13)

Samples of native, unpurified bovine (Friesan) cervical mucus were used. Samples were frozen in liquid nitrogen within 30 minutes of collection to minimise crystal size during ice formation and thus reduce disruption of gel structure. Mucus containing blood or contaminated by faeces were discarded.

Samples of Friesan semen, obtained in a frozen form, were stored under liquid nitrogen in individual 250 μl straws containing 20×10 sperm (8×10 viable).

A 0.9% (w/v) solution of compound (13) in aqueous sodium chloride was added to cervical mucus to give a 10 mM concentration of compound (13) in 0.75% gel, pH about 3.8, then 0.01M NaOH was added dropwise to the solution, to pH 7. Control samples were adjusted with saline only, to pH 7.

The prepared samples were loaded into flattened capillary tubes (2×80 mm, Camlab, UK) using a 1 ml hypodermic syringe and silicon tubing. After sealing one end of the tube with clingfilm, the tube was transferred to a 38° water bath such that sperm from a 50μl reservoir of the semen could ascend through the mucus. After 30 minutes, the tubes were removed and the sperm penetration through the mucus was assessed by measuring the distance from the origin of the first field of view, at ×300 magnification, in which the sperm count was less than 50.

Results for six tests are shown in Table 3. The mean distances of sperm penetration were significantly higher (Mann & Whitney U-test: p<0.05, n=6) for the control samples 11.3 (±2.7 SD) compared with those for the samples containing compound (13) 6.0 (±1.8 SD) respectively. Control samples contained sperm which demonstrated high speed flagellar strokes and head rotation and a strong directional component in their alignment. In contrast, 30–70% of sperm in the sample containing compound (13) were inert, whilst the remainder displayed a more aimless and weaker swimming activity.

TABLE 3

Effect of 10mM compound (13) corrected to pH7 on sperm penetration. Figures represent the distance (mm) from the origin to the first field of view yielding a sperm count of <50.

| Control | Compound (13) |
|---|---|
| 13.5 | 5.5 |
| 7.0 | 3.0 |
| 10.0 | 8.5 |
| 13.0 | 6.0 |
| 10.5 | 6.0 |
| 14.0 | 7.0 |

EXAMPLE 4

Spermicidal action of N-(2-dimethylaminoethyl)-1,3,8-trioxodecahydronaphthalene-2-carboxamide (13)

The spermicidal effects of compound (13) were investigated by introducing 50 μl of semen into 0.5 ml solutions of the same pH-adjusted solutions as in Example 3. The viability of sperm was then investigated at 15 and 40 minute times intervals under ×300 magnification. After the latter time point, control and test samples were centrifuged, the supernatant discarded, and the pellet resuspended in fresh saline to assess the reversibility of any spermicidal effects.

The results indicated that approximately 50% of control sperm were highly active after 15 minutes incubation. This figure is compatible with the proportion of viable sperm typically found in stored semen samples. However, in the test sample containing compound (13), 90% of sperm were inert whilst the remainder displayed slow and sporadic tail movements. After 40 minutes a slight reduction in the number of active control sperm had occurred but more than 40% still showed rapid motion, whereas the sperm in the test solution were 100% inert. On centrifugation and resuspension of sperm in clean saline, the number of active control sperm was reduced by 50%. No recovery of treated sperm was recorded on transfer to clean saline. Samples were observed for 30 minutes, after which more than 95% of control sperm became inactive.

We claim:

1. Compounds of the general formula

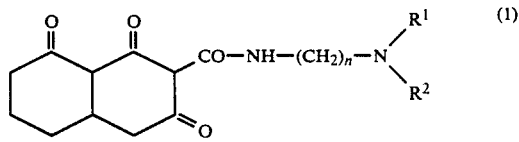

(1)

wherein n is from 1 to 6 and each of $R_1$ and $R_2$ represents an alkyl group of 1 to 4 carbon atoms, and their acid addition salts.

2. N-(2-dimethylaminoethyl)-1,3,8-trioxodecahydronaphthalene-2-carboxamide and its acid addition salts.

3. A method of contraception which comprises applying to the cervix of a female mammal capable of conception a sperm migration-inhibitory amount of a compound claimed in claim 1.

4. Compounds according to claim 1 wherein the acid addition salts are pharaceutically acceptable, for use in thickening gastro-intestinal mucus.

5. Compounds according to claim 4 wherein the gastro-intestinal mucus is oesophogal, stomach or duodenal mucus.

6. Compounds according to claim 1 wherein the acid addition salts are pharaceutically acceptable, for treating colitis or diverticulitis.

7. Compounds according to claim 1 wherein the acid addition salts are pharmaceutically acceptable for application to the eyes for treating "dry eye".

8. Compounds according to claim 1 for preventing pelvic inflammatory disease.

9. A method of treating the mammalian body by thickening mucus therein, said method comprising applying to the mammal at the site of the mucus or systematically a mucus-thickening amount of a compound claimed in claim 1.

10. The method of claim 9 wherein said application is systemic and said amount is effective for thickening gastro-intestinal mucus.

11. The method of claim 9 wherein said mucus is oesophegal, stomach or duodenal mucus.

* * * * *